United States Patent [19]

Habig et al.

[11] 4,338,473
[45] Jul. 6, 1982

[54] METHOD FOR REMOVING NITROSATION AGENT(S) FROM A NITRATED AROMATIC COMPOUND

[75] Inventors: Kurt Habig, Mörfelden; Konrad Baessler, Frankfurt am Main; Lothar Schulz, Eppstein; Heinz Schütte, Hofheim am Taunus, all of Fed. Rep. of Germany

[73] Assignee: Hoechst Aktiengesellschaft, Frankfurt am Main, Fed. Rep. of Germany

[21] Appl. No.: 151,286

[22] Filed: May 19, 1980

[30] Foreign Application Priority Data

May 21, 1979 [DE] Fed. Rep. of Germany ....... 2920448
Mar. 4, 1980 [DE] Fed. Rep. of Germany ....... 3008243

[51] Int. Cl.$^3$ ...................... C07C 76/02; C07C 79/10; C07C 79/12
[52] U.S. Cl. .................................................. 568/933
[58] Field of Search ........................ 568/933, 934, 935

[56] References Cited

U.S. PATENT DOCUMENTS

| | | | |
|---|---|---|---|
| 2,435,314 | 2/1948 | Kokatnur | 568/935 |
| 2,786,795 | 3/1957 | Ligett et al. | 568/933 |
| 3,169,150 | 2/1965 | Bachman | 568/937 |
| 3,409,620 | 11/1968 | Ohmam et al. | 568/933 |
| 4,028,425 | 6/1977 | Gilbert | 568/934 |
| 4,096,195 | 6/1978 | Schneider et al. | 568/933 |
| 4,110,405 | 8/1978 | Bornengo | 568/933 |
| 4,120,905 | 10/1978 | Cannon et al. | 568/933 |
| 4,180,679 | 12/1979 | Kapoor | 568/933 |

OTHER PUBLICATIONS

C.A., vol. 75, No. 13, 87406g, (1971).
C.A., vol. 73, No. 12, 62440j, (1970).
Vogel, A. I., Practical Organic Chemistry, Longmans, Green & Co., London, pp. 507–508, (1948).
The Merck Index, Eight Edition, Merck & Co., Inc., Rahway, N.J., p. 735, (1968).

Primary Examiner—Teddy S. Gron
Attorney, Agent, or Firm—Curtis, Morris & Safford

[57] ABSTRACT

Nitrosation agent(s), contained as by-products in nitrated aromatic compounds after nitration with nitric acid or nitration acid, are removed by a water treatment, wherein the water is distilled off at least partially in vapor form, advantageously under reduced pressure. In the further reaction of the nitrocompounds treated in this manner undesired nitrosamines are practically not formed. The process is especially suitable for the manufacture of 4-di-n-propylamino-3,5-dinitrobenzotrifluoride (Trifluralin), a valuable herbicide, substantially free from nitrosamine(s).

11 Claims, No Drawings

METHOD FOR REMOVING NITROSATION AGENT(S) FROM A NITRATED AROMATIC COMPOUND

"Nitrated aromatic compounds" in the sense of the present specification are aromatic nitrocompounds produced by nitration of corresponding aromatic starting compounds with concentrated nitric acid or with nitration acid (concentrated nitric acid/sulfuric acid) with subsequent conventional working up. The term "nitrated aromatic compounds" is not intended to include aromatic nitrocompounds which have been reacted further by reactions following the nitration.

Nitrated aromatic compounds are final and intermediate products in various fields, especially in the explosive sector, pharmaceutical sector and plant protection sector.

A nitrated aromatic compound important as an intermediate in the plant protection sector is, for example, 4-chloro-3,5-dinitrobenzotrifluoride, obtainable by nitration of p-chlorobenzotrifluoride, which can be reacted, for example, with di-n-propylamine to give the herbicide Trifluralin (4-di-n-propylamino-3,5-dinitrobenzotrifluoride). This synthesis can be illustrated by the following reaction scheme:

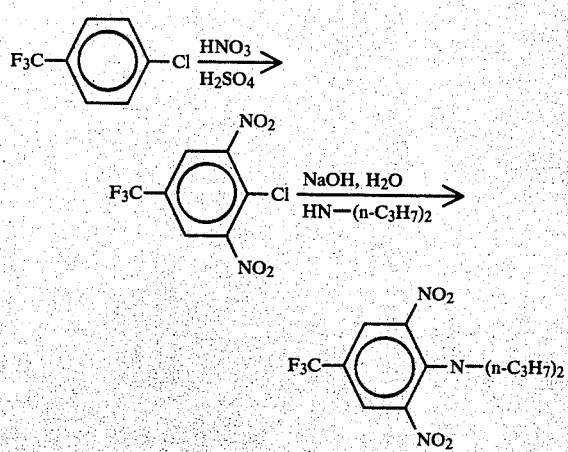

With modern analytical methods for minor amounts of nitrosamines have been found in the Trifluralin produced in this manner, which may display a carcinogenic effect at least in animals and which is highly undesirable (cf. DE-OS No. 2,835,530). It is assumed that the formation of said nitrosamines is a result of the nitrosation of di-n-propylamine used in the last reaction stage by nitrosation agents which are obviously contained in minor amounts in the precursor of the Trifluralin, i.e. in the 4-chloro-3,5-dinitrobenzotrifluoride, and originate from the nitration reaction.

Various processes have been developed to remove the nitrosamines from the Trifluralin as completely as possible. According to the process of DE-OS No. 2,831,119, for example, this is done by a treatment with 20 to 38% hydrochloric acid or with gaseous hydrogen chloride in liquid phase at temperatures of up to 140° C.

DE-OS No. 2,835,530 proposes a treatment with bromine, chlorine, N-bromosuccinimide, N-chlorosuccinimide, bromochloride, pyridineperbromide and/or pyridinium bromide-perbromide in order to reduce the nitrosamine concentration, while DE-OS No. 2,837,529 is concerned with a treatment with phosphorus or sulfur halides and oxyhalides or with TiCl$_4$.

At first, these methods lead to a satisfactory reduction of the nitrosamine values, but it is said that the values increase again after prolonged reaction time. Consequently, if the reaction time is not exactly optimized, the low nitrosamine values, possible according to the aforesaid methods, may not be obtained. Moreover, these methods involve an additional reaction step with the necessity of working up and recovering the reagents used.

Attempts have also been made to avoid the formation of nitrosamines by removing as quantitatively as possible the nitrosation agent from the nitrated precursor or Trifluralin, i.e., 4-chloro-3,5-dinitrobenzotrifluoride and contained therein as by-product (cf. DE-OS No. 2,840,551). To this end the precursor is
  (a) treated with an aqueous solution of an inorganic base having a temperature of from 50° to 100° C., whereupon the treated product may be separated,
  (b) an inert gas, for example air, is passed through an aqueous mixture of the product at the same temperature and
  (c) if necessary, stages (a) and/or (b) are repeated as often as desired.

By this treatment the content of nitrosation agent(s) in the 4-chloro-3,5-dinitrobenzotrifluoride is obviously reduced to such an extent that the Trifluralin obtained in the subsequent reaction with di-n-propylamine has a nitrosamine content which is almost as low as that obtained by the known processes of the direct nitrosamine removal from Trifluralin. If 4-chloro-3,5-dinitrobenzotrifluoride is treated with water only, i.e. in the absence of an inorganic base, at elevated temperature and while passing through an inert gas, the nitrosamine content in the Trifluralin is not or practically not reduced (cf. table of test results on page 16 of DE-OS No. 2,840,511). The process for the removal from nitrosation agent(s) from the Trifluralin precursor according to DE-OS No. 2,840,551 seems to be more favorable than the processes disclosed in DE-OS No. 2,831,119, DE-OS No. 2,835,530 and DE-OS No. 2,837,529 since a re-increase of the nitrosamine content in the Trifluralin is hardly to be feared, but the necessity to perform several process stages is disadvantageous in the case, too.

It has, therefore been desirable to develop a simple and economical process, while avoiding the disadvantages of the known processes, which makes it possible to produce nitrosamine-free Trifluralin either by removing the said nitrosamines from the Trifluralin or by avoiding the formation thereof and which can be used quite generally and not only for this special case.

This objective has been achieved in simple and satisfactory manner by a water treatment of 4-chloro-3,5-dinitrobenzotrifluoride at normal or elevated temperature wherein the water used is removed at least partially in vapor form. The process can be used not only for this special case but also for other nitrated aromatic compounds to remove nitrosation agent still contained therein from the nitration.

It is extremely surprising that by an at least partial removal of the water used for the water treatment of nitrated aromatic compounds the nitrosation agent can be removed, since, especially in view of the results summarized in the table on page 16 of DE-OS No. 2,840,551, it could hardly be expected that nitrosation agents contained in nitrated aromatic compounds from the nitration are removed by a water treatment without addition of any other substance (for example basic substances).

It is the object of the present invention to provide a method for removing nitrosation agent(s) from nitrated aromatic compounds by a water treatment, which comprises removing at least partially in vapor from the water used for the treatment.

Suitable nitrated aromatic compounds in the process of the invention are, in principle, all possible nitrated aromatic compounds as defined above, for example nitrobenzene, nitronaphtalene and the derivatives thereof, preferably, however, nitrated aromatic compounds of the general formula I

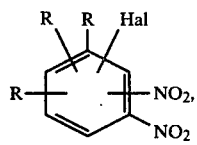

in which the radicals R, independently of one another, each is hydrogen, $C_1$-$C_4$ alkyl, $CF_3$, $SO_2NH_2$ or $SO_2CH_3$ and Hal denotes F, Cl, Br or I, preferably Cl or Br. More particularly, compounds of this type are, for example

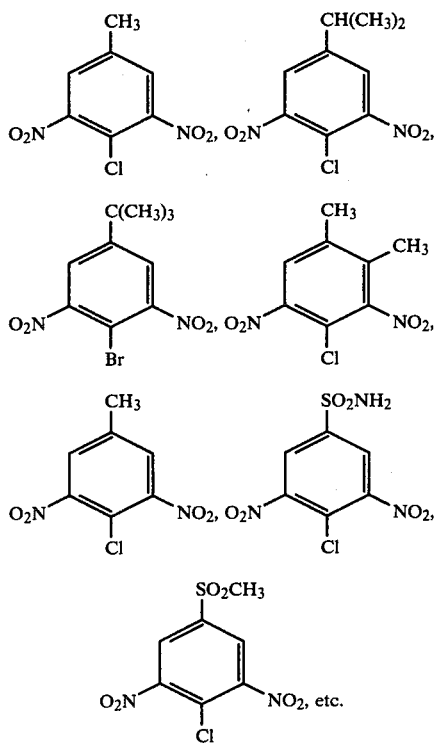

The method according to the invention is especially suitable for the treatment of 4-chloro-3,5-dinitrobenzotrifluoride, the precursor of Trifluralin.

According to a preferred embodiment the water treatment with simultaneous or subsequent, at least partial removal of the water in vapor form is carried out at a temperature of from about 80° to 120° C., preferably about 95° to 100° C. The amount of water used is not critical, but about 10 to 50% by weight, preferably about 20 to 40% by weight, of water, calculated on the nitrated aromatic compound, proved to be advantageous. According to the present preferred embodiment steam is passed through the nitrated aromatic compound to be treated (like in a steam distillation) or the nitrated aromatic compound is heated with water to a temperature in the aforesaid range, whereupon the water is distilled off at least partially, preferably in a weak vacuum, at about 95° to 100° C. In this case the nitrated aromatic compound is preferably treated in the liquid or molten state.

The water treatment with at least partial removal of the water in the vaporous form lasts preferably from about 10 to 60 minutes. Shorter or longer treatment times are also possible, depending on the quantity treated and the individual treatment conditions (temperature, rate of passing through steam or of water distillation), but in general they do not involve any special advantage.

According to another preferred embodiment, carried out under still milder conditions, the water treatment is carried out in the form of a crystallization from aqueous solution or emulsion under reduced pressure at temperatures down to room temperature.

It proved advantageous to remove at least a further portion of the water under reduced pressure from the aqueous crystal suspension obtained after crystallization from aqueous solution or emulsion under reduced pressure.

Contrary to the first described embodiment (to be carried out practically exclusively with liquid or molten nitrated aromatic compounds), the latter embodiment is carried out in the crystallization range of the respective nitrated aromatic compounds, that is to say in the range where they pass from the liquid into the solid state, and in the range where they are already solid.

In this latter embodiment it is essential that during crystallization from aqueous solution or emulsion the pressure is reduced so that the water can distil off. Therefore, the pressure must be below the vapor pressure of water at the respective temperature. If larger amounts of water are still present, the reduced pressure applied should not be too far below the water vapor pressure at the respective temperature in order to avoid undesired delay in boiling or the like.

As regards the reduced pressure to be applied, it is the same with the removal of water from the aqueous crystal suspension.

With consideration of the criteria described in this context, the pressure may be down to about 10 mbar. It is only necessary that a sufficient evaporation rate of water and an unhindered evaporation be ensured.

It is quite obvious that this embodiment of the process of the invention is unsuitable for nitrated aromatic compounds having a higher vapor pressure than water at the respective temperatures.

The temperatures of the latter embodiments are the same as in the first embodiment; they are in the range from about room temperature (about 20° C.) to 120° C. In each individual case the temperatures depend, of course, on the melting point of the nitrated aromatic compound; they are near this melting point and therebelow. Hence, in this case the temperature for the treatment of one and the same nitrated aromatic compound is lower than in the first embodiment wherein the nitrated aromatic compound is practically always in the liquid state. Temperatures below about 20° C. are, in principle, also possible, but they do not involve any advantage.

By the water treatment according to the invention with at least partial removal of the water in vapor form the nitrosation agents contained in the nitrated aromatic compounds as by-products from the nitration are obviously split, decomposed and/or removed with the water vapor.

When the nitrated aromatic compounds treated in the aforesaid manner are further reacted, for example with amines, practically no nitrosamines can be detected in the reaction products.

The process of the invention advantageously differs from the known processes for the removal of nitrosamines from corresponding reaction products and for the removal of nitrosation agent(s) from nitrated aromatic compounds in that it can be carried out in very simple manner without use of additional chemicals and without additional process steps. In general, the nitrated aromatic compounds are purified by washing with water so that the removal of nitrosation agent(s) according to the invention can normally be carried out in the same process step. Because of the possible lower temperatures, the second embodiment of the process of the invention can be carried out under milder conditions.

Hence, the invention offers a considerable progress.

The following examples illustrate the invention; the nitrosamine concentration was determined by the methods described in DE-OS No. 2,831,119.

EXAMPLE 1

(a) Production of Trifluralin in conventional manner:

2 Mols of p-chlorobenzotrifluoride were mononitrated in known manner and then dinitrated at 110° to 125° C. After dilution of the final acid to about 70% by weight sulfuric acid, the liquid nitroproduct was separated at 80° C. and washed repeatedly with water and a small amount of sodium hydroxide solution until it was neutral. 432 g of 4-chloro-3,5-dinitrobenzotrifluoride melting at 54.8° C. were obtained.

After the usual reaction with di-n-propylamine to give Trifluralin (yield almost quantitative, m.p. 46.2° C.), the reaction product was found to contain 29 ppm of nitroso-di-n-propylamine.

(b) Removal of nitrosation agent(s) from 4-chloro-3,5-dinitrobenzotrifluoride according to the first embodiment of the invention:

Steam was introduced for 10 minutes at about 100° C. into 500 g of 4-chloro-3,5-dinitrobenzotrifluoride (prepared as described in Example 1a). About 220 g of condensate were obtained which were reacted in usual manner to give Trifluralin. The product had a nitroso-di-n-propylamine content of 1 ppm.

(c) Removal of nitrosation agent(s) from the same precursor by the other preferred embodiment of the invention:

500 g of 4-chloro-3,5-dinitrobenzotrifluoride (prepared as described in Example 1a) were emulsified in 500 ml of water while thoroughly stirring at 70° C., the emulsion was cooled to 50° C. by partial evaporation under reduced pressure of the water and crystallized at the same temperature.

After further cooling to about 40° C., heating to 40° to 50° C. under reduced pressure was continued until a total amount of about 100 ml of water had distilled off.

After melting and water separation (for example by decantation), the product was reacted as usual with di-n-propylamine. The Trifluralin obtained had a nitroso-di-n-propylamine content of 1 ppm.

EXAMPLE 2

500 g of 4-chloro-3,5-dinitrobenzotrifluoride (prepared as described in Example 1a) and 220 g of water were heated to 98° to 100° C. The total amount of water was then distilled off under slightly reduced pressure and the product obtained was reacted to give Trifluralin in usual manner. The nitroso-di-n-propylamine content was found to be 2 ppm.

We claim:

1. A method for removing one or more nitrosation agents from 4-chloro-3,5-dinitrobenzotrifluoride by treatment with water, which comprises contacting water, without adding any other substance, with 4-chloro-3,5-dinitrobenzotrifluoride and one or more nitrosation agents, and removing water from the 4-chloro-3,5-dinitrobenzotrifluoride such that the removed water is at least partially in vapor form.

2. A method as claimed in claim 1, wherein about 10 to 50% by weight of water, calculated on the 4-chloro-3,5-dinitrobenzotrifluoride, is used for removal of said one or more agents.

3. A method as claimed in claim 1, wherein about 20 to 40% by weight of water, calculated on the 4-chloro-3,5-dinitrobenzotrifluoride, is employed in the water treatment.

4. A method as claimed in claim 1, which comprises passing steam through said 4-chloro-3,5-dinitrobenzotrifluoride and one or more nitrosation agents.

5. A method as claimed in claim 1, which comprises heating the 4-chloro-3,5-dinitrobenzotrifluoride and one or more nitrosation agents together with water, and distilling water off at a temperature of from about 95° to 100° C.

6. A method as claimed in claim 1, wherein the water treatment comprises crystallizing said 4-chloro-3,5-dinitrobenzotrifluoride from aqueous solution or emulsion under reduced pressure.

7. A method as claimed in claim 1, wherein the water removal is carried out at temperature of from about 80° to 120° C.

8. A method as claimed in claim 7, wherein the water removal is carried out at temperature of from about 95° to 100° C.

9. A method as claimed in claim 5, wherein said distillation is effected under slightly reduced pressure.

10. A method as claimed in claim 1, wherein the duration of the water treatment is about 10 to 60 minutes.

11. A method as claimed in claim 6, wherein, after crystallization from aqueous solution under reduced pressure, at least part of the water is removed from the crystal suspension under reduced pressure.

* * * * *